United States Patent [19]

Kawashima et al.

[11] Patent Number: 5,496,817
[45] Date of Patent: Mar. 5, 1996

[54] 3-OXO-1,4-BENZOTHIAZINE DERIVATIVES

[75] Inventors: Yoichi Kawashima, Kyoto; Atsutoshi Ota; Hiroyuki Mibu, both of Osaka, all of Japan

[73] Assignee: Santen Pharmaceutical Co., Ltd., Osaka, Japan

[21] Appl. No.: 211,940

[22] PCT Filed: Aug. 25, 1993

[86] PCT No.: PCT/JP93/01190

§ 371 Date: Apr. 22, 1994

§ 102(e) Date: Apr. 22, 1994

[87] PCT Pub. No.: WO94/05647

PCT Pub. Date: Mar. 17, 1994

[30] Foreign Application Priority Data

Aug. 31, 1992 [JP] Japan .................. 4-231669

[51] Int. Cl.⁶ .................. C07D 279/16; A61K 31/54
[52] U.S. Cl. .................. 514/224.2; 544/52; 514/63
[58] Field of Search .................. 544/52; 514/224.2, 514/63

[56] References Cited

U.S. PATENT DOCUMENTS 3,923,709  12/1975  Worley .................. 544/52

FOREIGN PATENT DOCUMENTS 0492667  7/1992  European Pat. Off. .

OTHER PUBLICATIONS

J. W. Worley et al, "2-Dialkylphosphonyl-and 2-alkylidene-3,4-dihydro-3-oxo-2H-1,4-benzothiazines", Journal of Organic Chemistry, vol. 40, No. 12, 13 Jun. 1975, Easton US, pp., 1731-1734.

*Primary Examiner*—John M. Ford
*Attorney, Agent, or Firm*—Frishauf, Holtz, Goodman, Langer & Chick

[57] ABSTRACT

This invention offers the compounds of the formula [I] which are useful for treatment of cataract.

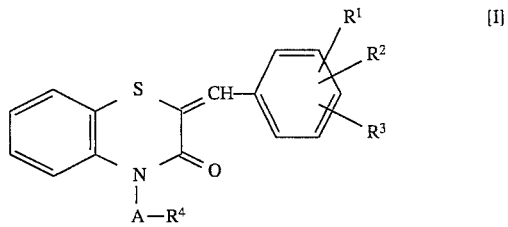

wherein $R^1$ is hydroxy which can be protected by a protective group;

$R^2$ is lower alkyl;

$R^3$ is hydrogen, lower alkyl, hydroxy, which can be protected by a protective group, or lower alkoxy, and the said lower alkyl can be substituted by hydroxy, which can be protected by a protective group, amino or lower alkylamino;

$R^4$ is carboxy which can be converted to ester or amide, and

A is alkylene.

12 Claims, No Drawings

3-OXO-1,4-BENZOTHIAZINE DERIVATIVES

This application is a 371 of PCT/JP93/01190, filed Aug. 25, 1993.

TECHNICAL FIELD

This invention relates to novel 3-oxo-1,4-benzothiazine derivatives which have protein stabilizing effect and suppressive effect on lipid peroxide formation, and are useful for treatment of cataract etc.

BACKGROUND OF THE INVENTION

Cataract is an intractable eye disease where an opacification of lens is caused and results in a loss of visual acuity. Various studies on a causal factor and mechanism of cataract, and a treatment method therefor have been made. But at present, there is very few medical substances which are effective for cataract.

It is reported that an increase of peroxide in lens is related to a cause of cataract and a chemical substance having suppressive effect on lipid peroxide formation is effective on treatment of cataract (Current Eye Res., 5, 37 (1986)). It is also reported that protein denaturation is observed in lenses of cataract patients (Ophthalmology, 19, 1283 (1977)).

From the reports, a chemical substance which has suppressive effect on lipid peroxide formation in combination with protein stabilizing effect can be presumed to be especially useful for treatment of cataract. A compound having the above both effects, however, has not been studied and a development of such compound has been desired.

As the result of our precise study to find a compound having suppressive effect on lipid peroxide formation in combination with protein stabilizing effect, the inventors found that 3-oxo-1,4-benzothiazine derivatives, in which the 2nd-position was substituted by a benzylidene group and the 4th-position was substituted by a carboxyalkyl group, and the phenyl ring of the said benzylidene group was further substituted by hydroxy and lower alkyl groups, had the both effects.

3-Oxo-1,4-benzothiazine derivatives having benzylidene substituent at the 2nd-position, the chemical structure is common to the basic structure of the compound of this invention, were reported to be applicable to a herbicide (U.S. Pat. No. 3,923,709), a tranquilizer (Japanese Patent Publication No. 10671/1974) or a synthetic intermediate of benzothiazepine derivatives (Japanese Unexamined Patent Publication No. 72875/1985). The chemical structure of the compound of this invention is of course different from the compounds disclosed in the above prior arts. Further the prior arts disclose neither protein stabilizing effect nor suppressive effect on lipid peroxide formation.

Japanese Unexamined Patent Publication No. 287077/1989 discloses2-benzylidene-3-oxo-1,4-benzothiazine derivatives which have active oxygen elimination effect or suppressive effect on lipid peroxide formation. In the publication, however, a substituent at the 4th-position is limited to lower alkyl group and protein stabilizing effect is not disclosed at all.

In the meantime, recently an utility of aldose reductase inhibitors for treatment of cataract attracts attention. The compound of this invention has also aldose reductase inhibiting effect and is very useful for treatment of cataract.

DISCLOSURE OF THE INVENTION

This invention relates to the compounds of the formula [I] and salts thereof,

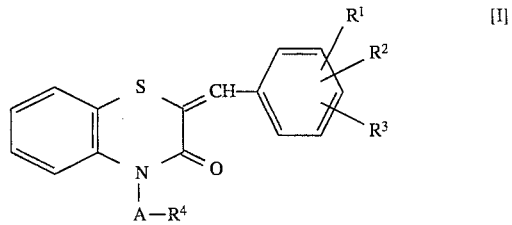

wherein
$R^1$ is hydroxy which can be protected by a protective group;
$R^2$ is lower alkyl;
$R^3$ is hydrogen, lower alkyl, hydroxy, which can be protected by a protective group, or lower alkoxy, and the said lower alkyl can be substituted by hydroxy, which can be protected by a protective group, amino or lower alkylamino;
$R^4$ is carboxy which can be converted into ester or amide, and
A is alkylene.
The same shall be applied hereinafter.

The terms defined above are explained as follows in more detail.

The term "lower alkyl" intends to designate straight or branched alkyl having 1 to 6 carbon atoms exemplified by methyl, ethyl, propyl, hexyl, isopropyl, tert.-butyl and (dimethyl)ethyl.

The term "lower alkoxy" intends to designate straight or branched alkoxy having 1 to 6 carbon atoms exemplified by methoxy, ethoxy, propoxy, hexyloxy, isopropoxy and tert.-butoxy.

The term "alkylene" intends to designate alkylene having 1 to 10 carbon atoms exemplified by methylene, ethylene, propylene, tetramethylene, heptamethylene, decamethylene, (dimethyl)methylene and (diethyl)methylene.

The term "a protective group" of hydroxy means a group widely used for protection of a hydroxy group, for example, lower alkylsulfonyl exemplified by methanesulfonyl; arylsulfonyl exemplified by phenylsulfonyl and p-toluenesulfonyl; lower alkanoyl exemplified by acetyl, propionyl and pivaloyl; lower alkoxymethyl exemplified by methoxymethyl; benzoyl; benzyloxymethyl; tetrahydropyranyl, or trimethylsilyl.

The term "ester" means an ester group widely used for a carboxylic acid, for example, lower alkyl ester exemplified by methyl ester, ethyl ester, isopropyl ester, butyl ester and hexyl ester, or aryl lower alkyl ester exemplified by benzyl ester.

The term "amide" means an amide group widely used for a carboxylic acid, for example, amide formed with ammonia; amide formed with lower alkylamine exemplified by methylamine, dimethylamine and ethylamine, or amide formed with aryl lower alkylamine exemplified by benzylamine.

The compound of this invention can be converted into salts with base. Examples of the pharmaceutically acceptable salts are alkali metal salts or alkaline earth metal salts exemplified by sodium, potassium and calcium salts, ammonium salt or organic amine salts exemplified by diethylamine and triethanolamine salts.

The typical synthetic methods of the compounds of this invention are shown in the following 1) and 2).

1)

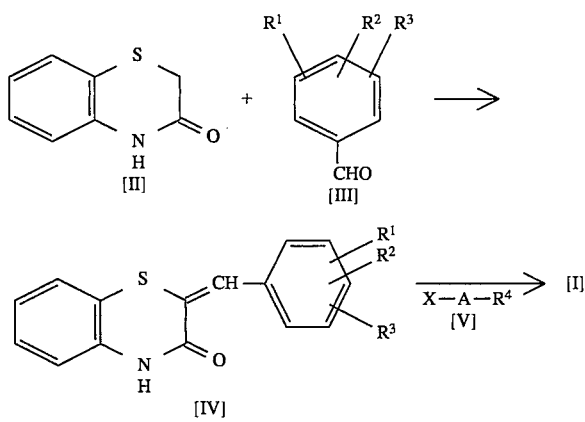

wherein X is halogen, alkylsulfonyl or arylsulfonyl.

The compound of the formula [IV] can be prepared by a reaction of the compound of the formula [II] with the compound of the formula [III] in the presence of base and a dehydrating agent. The compound of the formula [IV] is reacted with the compound of the formula [V] in the presence of base to give the compound of this invention of the formula [I]. In another way, the compound of the formula [IV] can be synthesized according to the method described in Japanese Unexamined Patent Publication No. 287077/1989.

2)

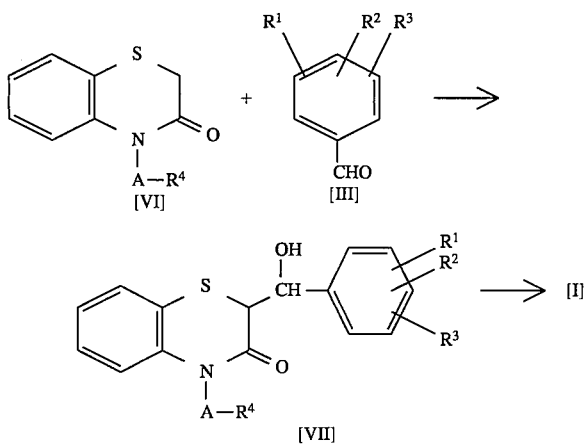

The compound of the formula [VII] can be prepared by a reaction of the compound of the formula [VI] with the compound of the formula [III] in the presence of base, and followed by dehydration to give the compound of this invention of the formula [I]. In another way, the compound of the formula [VI] can be synthesized according to the method reported by Raj Nandan Prasad et al. (Can. J. Chem., 44, 1247 (1966)).

A hydroxy group substituted in the phenyl ring of the benzylidene group may be protected by the above-mentioned protective group by the usual method before or after the reaction, and the protective group can be removed by the usual method.

A carboxyl group substituted in the 4th-position of benzothiazine can be converted into an ester or amide before or after the reaction by the usual method.

On the other hand, an ester or amide can be hydrolyzed to a carboxylic acid by the usual method.

The compounds prepared by the above methods can be converted into their salts as mentioned before by the usual method.

The compounds of this invention have stereoisomers or optical isomers, and these isomers are also included in this invention. For example, the compounds of this invention have Z-form or E-form because of the existence of benzylidene group, and these forms are included in this invention.

A compound which has suppressive effect on lipid peroxide formation in combination with protein stabilizing effect can be presumed to be especially useful for treatment of cataract. A compound having the above both effects, however, has not been studied and a development of such compound has been desired.

Based on the information that 3-oxo-1,4-benzothiazine derivatives having benzylidene substituent at the 2nd-position have suppressive effect on lipid peroxide formation (Japanese Unexamined Patent Publication No. 287077/1989), the inventors focused attention on compounds having 2-benzylidene-3-oxo-1,4-benzothiazine as basic structure and started a study to solve the above-mentioned problem.

First, the inventors paid attention to the information that toluene derivatives, in which hydroxy and tert.-butyl groups substituted, had anti-oxidizing effect. An anti-oxidizing agent shows suppressive effect on lipid peroxide formation. Accordingly the inventors studied how substituents play a role in suppressive effect on lipid peroxide formation by introducing various kinds of substituents such as alkyl and hydroxy into the phenyl ring of the benzylidene group. As the result of the study, it was found that a compound having an excellent suppressive effect on lipid peroxide formation could be obtained by introducing hydroxy and lower alkyl groups into the phenyl ring of the benzylidene group. But 2-benzylidene-3-oxo-1,4-benzothiazine compound substituted by lower alkyl group at the 4th-position, did not have protein stabilizing effect which is another necessary property. Therefore it was recognized that the substituent at the 4th-position exerted influence on protein stabilizing effect.

Accordingly the inventors synthesized novel compounds having various kinds of substituents at the 4th-position of 1,4-benzothiazine, and carried out examination to find a compound having protein stabilizing effect. As the result of the examination, the inventors found that the compound introduced carboxyalkyl substituent at the 4th-position had protein stabilizing effect.

From these studies, the inventors found that 2-benzylidene-3-oxo1,4-benzothiazine compound substituted by carboxyalkyl at the 4th-position did not show suppressive effect on lipid peroxide formation in combination with protein stabilizing effect until the phenyl ring of the benzylidene group was further substituted by hydroxy and lower alkyl groups. That is to say, the fundamental component of the compound of this invention is that the 4th-position of 3-oxo1,4-benzothiazine is substituted by a carboxyalkyl group and the 2nd-position is substituted by a benzylidene group, and the phenyl ring of the benzylidene group is further substituted by at least one hydroxy group and one lower alkyl group.

In case of a medical substance, a means of a conversion of a carboxylic acid group into an ester or protection of a hydroxy group by a suitable protective group is generally applied to make pro-drugs in order to enhance an absorption or improve a lasting time in a living body, or to make a compound stable in formation. Furthermore, such techniques are generally used for manufacturing drugs. In other words, such derived compound is generally used as a synthetic intermediate. Therefore in this invention, a hydroxy group may be protected by the widely used protective group for hydroxy, and a carboxy moiety of a carboxyalkyl group may be converted into an ester or amide, which is a general carboxylic acid derivative.

The characteristic structure of the compound of this invention is that explained in the above, but a preferable example of the substituent at the phenyl ring of the benzylidene group is explained as follows: a hydroxy group substitutes at the 4th-position, more preferably, lower alkyl group(s) substitute(s) at least one vicinal position of a hydroxy substituent. That is to say, it is preferable that lower alkyl group(s) substitute(s) at the 3rd-position or at the both of 3rd- and 5th-positions. More preferable example of the lower alkyl group is methyl or tert.-butyl.

In order to examine the effect of the compound of this invention, first of all, an experiment to examine protein stabilizing effect was performed using bovine serum albumin.

Details are shown in the article of Pharmacological Test. The inventors found that the compound of this invention had excellent protein stabilizing effect, however the compound which has different substituents in spite of the same basic structure as the compound of this invention, namely, 1,4-benzothiazine derivative having lower alkyl substituent at the 4th-position described in Japanese Unexamined Patent Publication No. 287077/1989, did not have protein stabilizing effect.

Secondary, in order to examine the suppressive effect on lipid peroxide formation of the compound of this invention, an experiment was performed using microsomes of rat liver. As the result of the experiment, it was found that the compound of this invention had excellent suppressive effect on lipid peroxide formation.

From the results of the above pharmacological tests, it was found that the compound of this invention had suppressive effect on lipid peroxide formation in combination with protein stabilizing effect, and was useful for treatment of cataract.

In addition, it is also reported that a chemical substance which has suppressive effect on lipid peroxide formation or protein stabilizing effect is applicable to an anti-inflammatory (Lancet, 2, 443 (1966)). Therefore it is expected that the compound of this invention is also useful for anti-inflammatory.

Furthermore, an experiment was carried out according to the report of Karo et al. (Chem. Pharm. Bull., 33, (1) 74–83 (1985)), and it was also found that the compound of this invention had an aldose reductase inhibiting effect.

This result further supports that the compound of this invention is excellent therapeutic agent for cataract and it is also expected to be useful for treatment of diabetic complications.

The compound of this invention can be administered orally or parenterally. Examples of dosage forms are tablet, capsule, granule, powder, injection, ophthalmics, etc. The preparations can be prepared by the usual method. For example, oral preparations such as tablet, capsule, soft capsule and granule can be produced, if necessary, by adding diluent such as lactose, starch, crystalline cellulose or vegetable oil; lubricant such as magnesium stearate or talc; binder such as hydroxypropylcellulose or polyvinylpyrrolidone; disintegrator such as carboxymethylcellulose calcium, or coating agent such as hydroxypropylmethylcellulose. Ophthalmics can be prepared by adding tonicity agent such as sodium chloride; buffer such as sodium phosphate; solubilizer such as polysorbate 80, or preservatives such as benzalkonium chloride.

The dosage is adjusted depending on symptom, age, dosage form, etc., but in the case of oral preparations, the usual daily dosage is 1 to 5000 mg, which can be given in one or a few divided doses. In the case of ophthalmics, the dosage is 0.001 to 5% and one to several drops can be instilled per day.

Examples of preparations and formulations of the compounds of this invention are shown below. These examples would not limit the scope of this invention, but are intended to make more clearly understand this invention.

EXAMPLE

REFERENCE EXAMPLE 1

2-(4-Acetoxy-3,5-dimethylbenzylidene)-3,4-dihydro-3-oxo-2H-1,4-benzothiazine (Reference compound No. 1-1)

Triethylamine (33.74 ml) was added to a suspension of 3,4-dihydro-3-oxo-2H-1,4-benzothiazine (4.0 g) and 3,5-dimethyl-4-hydroxybenzaldehyde (3.64 g) in acetic anhydride (114.2 ml). After the addition, the mixture was refluxed for 19 hours under nitrogen atmosphere. The reaction mixture was poured into 1N hydrochloric acid and the whole was extracted with ethyl acetate. The organic layer was washed with 1N sodium hydroxide and saturated sodium chloride solution, dried over anhydrous sodium sulfate and concentrated in vacuo. The oily residue was purified by silica gel column chromatography to give 1.3 g (16%) of the titled compound as crystals.

mp 231°–234° C.

IR (KBr, cm$^{-1}$) 3177, 3036, 2978, 1751, 1665, 1592, 1571, 1488, 1437, 1427, 1370, 1229, 1206, 1142, 1045

Following compounds can be prepared by the similar method as Reference Example 1.

2-(4-Acetoxy-3-tert.-butylbenzylidene)-3,4-dihydro-3-oxo-2H-1,4-benzothiazine (Reference compound No.1-2)

mp 230°–233° C.

IR (KBr, cm$^{-1}$) 3176, 3102, 3043, 2959, 1760, 1654, 1590, 1485, 1453, 1426, 1367, 1284, 1221, 1188, 1084

2-(4-Acetoxy-3-methoxy-5-methylbenzylidene)-3,4-dihydro-3-oxo-2H-1,4-benzothiazine (Reference compound No. 1–3)

mp 230°–231° C.

IR (KBr, cm$^{-1}$) 3176, 3037, 2977, 1759, 1665, 1592, 1488, 1462, 1426, 1373, 1338, 1280

REFERENCE EXAMPLE 2

2-(5-tert.-Butyl-3-dimethylaminomethyl-4-hydroxybenzylidene)-3,4-dihydro-3-oxo-2H-1,4-benzothiazine (Reference compound No. 2-1)

(1) To a solution of 2-(4-acetoxy-3-tert.-butylbenzylidene)-3,4-dihydro-3-oxo-2H-1,4-benzothiazine (Reference compound No. 1–2, 0.31 g) in the mixture of tetrahydrofuran (12 ml) and methanol (3 ml), lithium hydroxide (0.18 g) dissolved in water (8 ml) was added dropwise under ice cooling. After the addition, the mixture was stirred for additional 10 minutes. The reaction mixture was poured into 1N hydrochloric acid and the whole was extracted with ethyl acetate. The organic layer was washed with saturated sodium chloride solution, dried over anhydrous sodium sulfate and concentrated in vacuo to give 0.25 g (91%) of 2-(3-tert.-butyl-4-hydroxybenzylidene)-3,4-dihydro-3-oxo-2H-1,4-benzothiazine as crystals.

mp 239°–241° C.

IR (KBr, cm$^{-1}$) 3161, 3094, 3032, 2956, 1639, 1584, 1500, 1482, 1420, 1375

(2) 2-(3-tert.-butyl-4-hydroxybenzylidene)-3,4-dihydro-3-oxo-2H-1,4-benzothiazine (0.25 g) dissolved in ethanol (5 ml) was added to a mixture of 37% aqueous formaldehyde solution (0.09 g), 40% aqueous dimethylamine solution (0.13 g) and ethanol (10 ml). After the addition, the mixture was refluxed for 4 hours. The resulting crystals were collected by filtration to give 0.21 g (71%) of the titled compound.

mp 223°–227° C.

IR (KBr, cm$^{-1}$) 3176, 3043, 2957, 1660, 1590, 1569, 1487, 1469, 1445, 1426, 1407, 1365, 1306, 1290

REFERENCE EXAMPLE 3

2-[5-tert.-Butyl-3-[1,1-dimethyl-2-(tetrahydropyran-2-yloxy)ethyl]-4-hydroxy-α-(tetrahydropyran-2-yloxy)benzyl] -3,4-dihydro-3-oxo-2H-1,4-benzothiazine (Reference compound No. 3-1)

(1) To a solution of diisopropylamine (3.8 ml) in tetrahydrofuran (20 ml), 1.6 M n-butyllithium in n-hexane (17.1 ml) was added under argon atmosphere and dry ice-methanol cooling. After the addition, the mixture was stirred for additional 30 minutes. To the stirred mixture, 3,4-dihydro-3-oxo-2H-1,4-benzothiazine (1.13 g) dissolved in tetrahydrofuran (50 ml) and hexamethylphosphoramide (8 ml) were added dropwise under dry ice-methanol cooling. The reaction mixture was stirred additionally for 15 minutes. Then 3-tert.-butyl-5-(1,1-dimethyl-2-hydroxyethyl)-4-hydroxybenzaldehyde (1.71 g) dissolved in tetrahydrofuran (15 ml) was added to the reaction mixture, and the mixture was stirred additionally for 1.5 hours. To the reaction mixture, aqueous ammonium chloride solution was added and the whole was extracted with ethyl acetate. The organic layer was washed with saturated sodium chloride solution, dried over anhydrous sodium sulfate and concentrated in vacuo. The oily residue was purified by silica gel column chromatography to give 1.63 g (7.3%) of erythro-2-[5-tert.-butyl-3-(1,1-dimethyl-2-hydroxyethyl)-α,4-dihydroxybenzyl]-3,4-dihydro-3-oxo-2H-1,4-benzothiazine.

IR (KBr, cm$^{-1}$) 2963, 1676, 1586, 1481, 1298, 1197, 985, 752.

(2) Dihydropyran (0.024 g) dissolved in tetrahydrofuran (2.3 ml) and pyridinium p-toluenesulfonate (0.004 g) were added to a solution of erythro-2-[5-tert.-butyl-3-(1,1-dimethyl-2-hydroxyethyl)-α,4-dihydroxybenzyl]-3,4-dihydro-3-oxo-2H-1,4-benzothiazine (0.029 g) in dichloromethane (1 ml).

After the addition, the reaction mixture was refluxed for one day. To the mixture, saturated sodium chloride solution was added and the whole was extracted with dichloromethane. The organic layer was dried over anhydrous sodium sulfate and concentrated in vacuo. The oily residue was purified by silica gel column chromatography to give 0.026 g (62.7%) of the titled compound.

IR (Film, cm$^{-1}$) 3248, 2948, 2247, 1674, 1586, 1480, 1435, 1388, 1355, 1203, 1120, 1059, 1034, 910

EXAMPLE 1

2-(3,5-Di-tert.-butyl-4-hydroxybenzylidene)-3,4-dihydro-4-ethoxycarbonylmethyl-3-oxo-2H-1,4-benzothiazine (Compound No. 1-1)

To a stirred solution of 2-(3,5-di-tert.-butyl-4-hydroxybenzylidene)-3,4-dihydro-3-oxo-2H-1,4-benzothiazine (0.5 g) in tetrahydrofuran (7 ml), 1.6 M n-butyllithium in n-hexane (1.64 ml) was added dropwise under ice-sodium chloride cooling. Ethyl bromoacetate (0.15 ml) dissolved in tetrahydrofuran (2 ml) was added dropwise to the mixture, and the mixture was stirred over night at room temperature. The reaction mixture was poured into aqueous saturated ammonium chloride solution and the whole was extracted with ethyl acetate. The organic layer was dried over anhydrous sodium sulfate and concentrated in vacuo. The oily residue was purified by silica gel column chromatography to give 0.36 g (58.1%) of the titled compound.

IR (KBr, cm$^{-1}$) 3620, 2957, 1750, 1649, 1590, 1486, 1421, 1363, 1197, 1021, 747

Following compounds can be prepared by the similar method as Example 1.

2-(3,5-Di-tert.-butyl-4-hydroxybenzylidene)-3,4-dihydro-4-methoxycarbonylmethyl-3-oxo-2H-1,4-benzothiazine (Compound No. 1-2)

mp 158°–160° C.

IR (KBr, cm$^{-1}$) 3606, 2959, 1763, 1747, 1634, 1590, 1570, 1486, 1434, 1368, 1207, 1142, 763

4-Butoxycarbonylmethyl-2-(3,5-di-tert.-butyl-4-hydroxybenzylidene)-3,4-dihydro-3-oxo-2H-1,4-benzothiazine (Compound No. 1-3)

mp 143°–144° C.

IR (KBr, cm$^{-1}$) 3605, 2959, 1754, 1738, 1642, 1590, 1568, 1488, 1434, 1363, 1266, 1208, 1142, 756

2-(3,5-Di-tert.-butyl-4-hydroxybenzylidene)-3,4-dihydro-4-(3-ethoxycarbonylpropyl)-3-oxo-2H-1,4-benzothiazine (Compound No. 1-4)

IR (Film, cm$^{-1}$) 3624, 2959, 1731, 1644, 1589, 1485, 1442, 1373, 1209, 750

2-(3,5-Di-tert.-butyl-4-hydroxybenzylidene)-3,4-dihydro-4-(7-methoxycarbonylheptyl)-3-oxo-2H-1,4-benzothiazine (Compound No. 1-5)

IR (Film, cm$^{-1}$) 3626, 2952, 1732, 1644, 1589, 1484, 1443, 1372, 1210, 751

2-(3,5-Di-tert.-butyl-4-methanesulfonyloxybenzylidene)-3,4-dihydro-4-ethoxycarbonylmethyl-3-oxo-2H-1,4-benzothiazine (Compound No. 1-6)

2-(4-Acetoxy-3,5-dimethylbenzylidene)-3,4-dihydro-4-ethoxycarbonylmethyl-3-oxo-2H-1,4-benzothiazine (Compound No. 1-7)

mp 83°–85° C.

IR (KBr, cm$^{-1}$) 3058, 2973, 1742, 1642, 1590, 1557, 1491, 1444, 1422, 1366, 1316, 1290, 1267

2-(4-Acetoxy-3-methoxy-5-methylbenzylidene)-3,4-dihydro-4-ethoxycarbonylmethyl-3-oxo-2H-1,4-benzothiazine (Compound No. 1-8)

IR (Film, cm$^{-1}$) 3478, 2982, 1748, 1650, 1592, 1487, 1447, 1416, 1368, 1324

2-(4-Acetoxy-3-tert.-butylbenzylidene)-3,4-dihydro-4-ethoxycarbonylmethyl-3-oxo-2H-1,4-benzothiazine (Compound No. 1-9)

IR (Film, cm$^{-1}$) 2960, 2870, 1752, 1654, 1591, 1487, 1447, 1419, 1395, 1368, 1324

2-(5-tert.-Butyl-3-dimethylaminomethyl-4-hydroxybenzylidene)-3,4-dihydro-4-ethoxycarbonylmethyl-3-oxo-2H-1,4-benzothiazine (Compound No. 1-10)

IR (Film, cm$^{-1}$) 2953, 1749, 1650, 1589, 1446, 1361, 1309, 1286, 1264, 1202, 1138, 1021

2-[5-tert.-Butyl-3-(1,1-dimethyl-2-hydroxyethyl)-4-hydroxybenzylidene]-3,4-dihydro-4-ethoxycarbonylmethyl-3-oxo-2H-1,4-benzothiazine (Compound No. 1-11)

IR (Film, cm$^{-1}$) 3408, 3118, 2960, 1746, 1632, 1588, 1485, 1422, 1327, 1266, 1203, 909, 733

EXAMPLE 2

4-Carboxymethyl-2-(3,5-di-tert.-butyl-4-hydroxybenzylidene)-3,4-dihydro-3-oxo-2H-1,4-benzothiazine (Compound No. 2-1)

Lithium hydroxide monohydrate (1.39 g) dissolved in water (25 ml) was added to a solution of 2-(3,5-di-tert.-butyl-4-hydroxybenzylidene)-3,4-dihydro-4-ethoxycarbonylmethyl-3-oxo-2H-1,4-benzothiazine (Compound No. 1-1, 0.31 g) in a mixture of tetrahydrofuran (40 ml) and methanol (10 ml). After the addition, the mixture was stirred for 2.5 hours at 5°–10° C. To the reaction mixture, 6N hydrochloric acid (6.5 ml) was added to acidify it. The mixture was concentrated in vacuo and extracted with ethyl acetate. The organic layer was washed with saturated sodium chloride solution, dried over anhydrous sodium sulfate and concentrated in vacuo to give 0.19 g (65.2%) of the titled compound as crystals.

mp 219°–221° C. (n-hexane-diisopropyl ether)

IR (KBr, cm$^{-1}$) 3611, 3081, 2958, 1729, 1622, 1588, 1559, 1492, 1420, 1365, 1316, 1270, 1206, 1183, 1142, 750

Following compounds can be prepared by the similar method as Example 2.

4-(3-Carboxypropyl)-2-(3,5-di-tert.-butyl-4-hydroxybenzylidene)-3,4-dihydro-3-oxo-2H-1,4-benzothiazine (Compound No. 2-2)

mp 162°–163° C. (diisopropyl ether)

IR (KBr, cm$^{-1}$) 3615, 3197, 2951, 1732, 1622, 1589, 1488, 1436, 1377, 1263, 1194, 1163, 751

4-(7-Carboxyheptyl)-2-(3,5-di-tert.-butyl-4hydroxybenzylidene)-3,4-dihydro-3-oxo-2H-1,4-benzothiazine (Compound No. 2-3)

mp 143°–144° C. (diisopropyl ether)

IR (KBr, cm$^{-1}$) 3558, 2952, 1708, 1641, 1592, 1482, 1434, 1369, 1314, 1211, 1114, 754

2-(5-tert.-Butyl-3-dimethylaminomethyl-4-hydroxybenzylidene)-4-carboxymethyl-3,4-dihydro-3-oxo-2H-1,4-benzothiazine (Compound No. 2-4)

mp 167°–171° C. (dec., hexane-ethyl acetate)

IR (KBr, cm$^{-1}$) 2954, 2783, 2706, 1736, 1630, 1591, 1485, 1446, 1424, 1364, 1326, 1304, 1285, 1262, 1188

EXAMPLE 3

4-Carbamoylmethyl-2-(3,5-di-tert.-butyl-4-hydroxybenzylidene)-3,4-dihydro-3-oxo-2H-1,4-benzothiazine (Compound No.3-1)

0.1N hydrochloric acid in methanol (3 ml) was added to a solution of 2-(3,5-di-tert.-butyl-4-hydroxybenzylidene)-3,4-dihydro-4-ethoxycarbonylmethyl-3-oxo-2H-1,4-benzothiazine (Compound No. 1-1, 0.4 g) in 17.85 N ammonia in methanol (15 ml). After the addition, the mixture was stirred for 4 days at 80° C. in a sealed tube and followed by concentration in vacuo. To the residue, dilute hydrochloric acid was added and the whole was extracted with ethyl acetate. The organic layer was dried over anhydrous sodium sulfate and concentrated in vacuo. The oily residue was purified by silica gel column chromatography to give 0.14 g (37.3%) of the titled compound.

mp 137°–144° C. (diisopropyl ether-benzene)

IR (KBr, cm$^{-1}$) 3590, 3463, 3305, 3187, 2958, 1647, 1590, 1485, 1421, 1198, 1114, 748, 679

Following compounds can be prepared by the similar method as Example 3.

2-(3,5-Di-tert.-butyl-4-hydroxybenzylidene)-3,4-dihydro-4-(N-methylcarbamoylmethyl)-3-oxo-2H-1,4-benzothiazine (Compound No. 3-2)

2-(3,5-Di-tert.-butyl-4-hydroxybenzylidene)-3,4-dihydro-4-(N,N-dimethylcarbamoylmethyl)-3-oxo-2H-1,4-benzothiazine (Compound No.3-3)

4-(N-Benzylcarbamoylmethyl)-2-(3,5-di-tert.-butyl-4-hydroxybenzylidene)-3,4-dihydro-3-oxo-2H-1,4-benzothiazine (Compound No. 3-4)

EXAMPLE 4

2-(3,5-Di-tert.-butyl-4-methoxymethoxybenzylidene)-3,4-dihydro-4-ethoxycarboxymethyl-3-oxo-2H-1,4-benzothiazine (Compound No. 4-1)

2-(3,5-di-tert.-butyl-4-hydroxybenzylidene)-3,4-dihydro-4-ethoxycarbonylmethyl-3-oxo-2H-1,4-benzothiazine (Compound No. 1-1, 0.35 g) dissolved in dimethylformamide (3 ml) is added to a stirred suspension of 60% sodium hydride suspension in mineral oil (0.03 g) in dimethylformamide (1 ml). The reaction mixture is stirred for additional 10 minutes under nitrogen atmosphere. To the mixture, a solution of chloromethyl methyl ether (0.3 ml) in dimethylformamide (1 ml) is added, and the mixture is stirred for 4 hours at 50° C. To the reaction mixture, water is added and the whole is extracted with ethyl acetate. The organic layer is dried over anhydrous sodium sulfate and concentrated in vacuo. The oily residue was purified by silica gel column chromatography to give the titled compound.

Following compound can be prepared by the similar method as Example 4.

2-(4-Benzyloxymethoxy-3,5-di-tert.-butylbenzylidene)-3,4-dihydro-4-ethoxycarboxymethyl-3-oxo-2H-1,4-benzothiazine (Compound No. 4-2)

EXAMPLE 5

2-(3,5-Di-tert.-butyl-4-trimethylsilyloxybenzylidene)-3,4-dihydro-4-ethoxycarbonylmethyl-3-oxo-2H-1,4-benzothiazine (Compound No. 5-1)

1,1,1,3,3,3-hexamethyldisilazane (1.7 ml) and chlorotrimethylsilane (1.4 ml) are added to a solution of 2-(3,5-di-tert.-butyl-4-hydroxybenzylidene)-3,4-dihydro-4-ethoxycarbonylmethyl-3-oxo-2H-1,4-benzothiazine (Compound No. 1-1, 0.53 g) in dimethylformamide (10 ml). After the addition, the mixture is refluxed for 3 days. To the reaction mixture, water is added and the whole is extracted with diethyl ether. The organic layer is dried over anhydrous sodium sulfate and concentrated in vacuo. The oily residue is purified by silica gel column chromatography to give the titled compound.

EXAMPLE 6

2-(4-Acetoxy-3,5-di-tert.-butylbenzylidene)-3,4-dihydro-4-methoxycarbonylmethyl-3-oxo-2H-1,4-benzothiazine (Compound No. 6-1)

Acetic anhydride (5.8 ml) and triethylamine (2.1 ml) are added to 2-(3,5-di-tert.-butyl-4-hydroxybenzylidene)-3,4-dihydro-4-methoxycarbonylmethyl-3-oxo-2H-1,4-benzothiazine (Compound No. 1-2, 0.80 g). After the addition, the mixture is refluxed over night. To the reaction mixture, dilute hydrochloric acid is added and the whole is extracted with ethyl acetate. The organic layer is dried over anhydrous sodium sulfate and concentrated in vacuo. The oily residue is purified by silica gel column chromatography to give the titled compound.

Following compound can be prepared by the similar method as Example 6.

2-(4-Benzoyloxy-3,5-di-tert.-butylbenzylidene)-3,4-dihydro-4-methoxycarbonylmethyl-3-oxo-2H-1,4-benzothiazine (Compound No. 6-2)

EXAMPLE 7

4-Carboxymethyl-2-(3,5-di-tert.-butyl-4-hydroxybenzylidene)-3,4-dihydro-3-oxo-2H-1,4-benzothiazine (Compound No. 2-1)

Potassium hydroxide (0.58 g) dissolved in water (10 ml) was added to a solution of 2-(4-acetoxy-3,5-di-tert.-butylbenzylidene)-3,4-dihydro-4-methoxycarbonylmethyl-3-oxo-2H-1,4-benzothiazine (Compound No. 6-1, 0.35 g) in ethanol (10 ml). After the addition, the mixture was refluxed over night. To the reaction mixture, 6N hydrochloric acid was added to acidify it. The mixture was concentrated in vacuo and extracted with ethyl acetate. The organic layer was dried over anhydrous sodium sulfate and concentrated in vacuo. The resulting crystals were collected by filtration. The physical properties of obtained compound were the same as those of the Compound No. 2-1 prepared in Example 2.

EXAMPLE 8

4-Carboxymethyl-3,4-dihydro-2-(3,5-dimethyl-4-hydroxybenzylidene)-3-oxo-2H-1,4-benzothiazine (Compound No.8-1) and 3,4-Dihydro-2-(3,5-dimethyl-4-hydroxybenzylidene)-4-methoxycarbonylmethyl-3-oxo-2H-1,4-benzothiazine (Compound No. 8-2)

To a solution of 2-(4-acetoxy-3,5-dimethylbenzylidene)-3,4-dihydro-4-ethoxycarbonylmethyl-3-oxo-2H-1,4-benzothiazine (Compound No. 1-7, 0.63 g) in tetrahydrofuran (5 ml), lithium hydroxide monohydrate (3.11 g) dissolved in water (13 ml) and methanol (2 ml) were added under ice cooling. After the addition, the mixture was stirred for additional 1.5 hours. To the reaction mixture, hydrochloric acid was added to acidify it and the whole was extracted with diethyl ether. The organic layer was washed with saturated sodium chloride solution, dried over anhydrous sodium sulfate and concentrated in vacuo. The oily residue was purified by silica gel column chromatography to give 0.33 g (63%) of the Compound No. 8-1 and 0.05 g (9%) of the Compound No. 8-2.

The physical properties of the Compound No.8-1
mp 213°–215° C. (hexane-ethyl acetate)
IR (KBr, $cm^{-1}$) 3441, 3008, 1749, 1589, 1576, 1537, 1487, 1447, 1428, 1388, 1324, 1291

The physical properties of the Compound No. 8-2
mp 171°–172° C.
IR (KBr, $cm^{-1}$) 3374, 3009, 2956, 1744, 1627, 1586, 1558, 1486, 1436, 1371, 1328, 1291, 1271, 1219

Following compounds can be prepared by the similar method as Example 8.

2-(3-tert.-Butyl-4-hydroxybenzylidene)-4-carboxymethyl-3,4-dihydro-3-oxo-2H-1,4-benzothiazine (Compound No. 8-3)
mp 214°–215° C. (dec., hexane-benzene)
IR (KBr, $cm^{-1}$) 3412, 3089, 2951, 1740, 1633, 1590, 1573, 1502, 1484, 1446, 1416

4-Carboxymethyl-3,4-dihydro-2-(4-hydroxy-3-methoxy-5-methylbenzylidene)-3-oxo-2H-1,4-benzothiazine (Compound No. 8-4)
mp 195°–197° C. (hexane-benzene)
IR (KBr, $cm^{-1}$) 3376, 2960, 1716, 1637, 1588, 1494, 1443, 1290, 1252, 1218

EXAMPLE 9

2-[5-tert.-Butyl-3-[1,1-dimethyl-2-(tetrahydropyran-2-yloxy)ethyl]-4-hydroxybenzylidene]-3,4-dihydro-4-ethoxycarbonylmethyl-3-oxo-2H-1,4-benzothiazine (Compound No. 9-1)

To a suspension of 60% sodium hydride suspension in mineral oil (0.10 g) in tetrahydrofuran (2 ml), 2-[5-tert.-butyl-3-[1,1-dimethyl-2-(tetrahydropyran-2-yloxy)ethyl]-4-hydroxy-α-(tetrahydropyran-2-yloxy)benzyl]-3,4-dihydro-3-oxo-2H-1,4-benzothiazine (Reference compound No. 3-1, 0.65 g) dissolved in tetrahydrofuran (2 ml) was added dropwise under nitrogen atmosphere and ice cooling. The mixture was stirred for additional 10 minutes. To the mixture, ethyl bromoacetate (0.19 ml) dissolved in tetrahydrofuran (2 ml) was added. After the addition, the mixture was stirred over night at room temperature. To the reaction mixture, aqueous ammonium chloride solution was added and the whole was extracted with ethyl acetate. The organic layer was washed with saturated sodium chloride solution, dried over anhydrous sodium sulfate and concentrated in vacuo. The oily residue was purified by silica gel column chromatography to give 0.59 g (93.3%) of the titled compound.

IR (Film, $cm^{-1}$) 3216, 2952, 1750, 1651, 1590, 1486, 1423, 1366, 1264, 1203, 1036, 901, 733

EXAMPLE 10

2-[5-tert.-Butyl-3-(1,1-dimethyl-2-hydroxyethyl)-4-hydroxybenzylidene]-4-carboxymethyl-3,4-dihydro-3-oxo-2-H1,4-benzothiazine (Compound No. 10-1)

p-toluenesulfonic acid (0.02 g) was added to a solution of 2-[5-tert.-butyl-3-[1,1-dimethyl-2-(tetrahydropyran-2-yl)oxyethyl]-4-hydroxybenzylidene]-3,4-dihydro-4-ethoxycarbonylmethyl-3-oxo-2H-1,4-benzothiazine (Compound No. 9-1, 0.54 g) in a mixture of methanol (5 ml) and chloroform (1 ml). After the addition, the mixture was stirred for 2.5 hours at 40° C. To the reaction mixture, saturated aqueous sodium hydrogencarbonate solution was added and the whole was extracted with ethyl acetate. The organic layer was concentrated in vacuo and the oily residue was dissolved in tetrahydrofuran (15 ml). To the solution, sodium hydroxide monohydrate (1.0 g) dissolved in water (15 ml) and methanol (5 ml) were added and the mixture was stirred for 1.5 hours under ice cooling. The reaction mixture was acidified with hydrochloric acid and extracted with ethyl acetate. The organic layer was washed with saturated sodium chloride solution, dried over anhydrous sodium sulfate and concentrated in vacuo. The oily residue was purified by silica gel column chromatography to give 0.16 g (36.9%) of the titled compound.

mp 216°–217° C. (dec., diisopropyl ether-ethyl acetate)
IR (KBr, $cm^{-1}$) 3460, 2958, 1735, 1606, 1587, 1548, 1419, 1371, 1268, 1193, 747

FORMULATION

Examples of the formulations of the compounds of this invention are shown below.

| Tablet | |
|---|---|
| compound of this invention | 10 mg |
| lactose | 123 mg |
| crystalline cellulose | 35 mg |
| hydroxypropylcellulose | 2 mg |
| magnesium stearate | 1 mg |
| total | 170 mg |
| compound of this invention | 50 mg |
| lactose | 140 mg |
| crystalline cellulose | 45 mg |
| polyvinylpyrrolidone | 3 mg |
| magnesium stearate | 2 mg |
| total | 240 mg |

| Granule | |
|---|---|
| compound of this invention | 5 mg |
| lactose | 485 mg |
| polyvinylpyrrolidone | 8 mg |
| magnesium stearate | 2 mg |
| total | 500 mg |

PHARMACOLOGICAL TEST

In order to study the utilities of the compounds of this invention, protein stabilizing effect and suppressive on lipid peroxide formation were examined.

13
1. Protein Stabilizing Effect

As a method of examining protein stabilizing effect, the method of measuring an effect of a compound on the stability of bovine serum albumin against heat coagulation is known (Lancet, 2, 443 (1966)).

Protein stabilizing effect of the compound of this invention was examined according to the method described in the above-mentioned journal.

Experimental Method

Under ice cooling, bovine serum albumin (Sigma Chemical Company) was dissolved in 0.2 M potassium phosphate buffer solution (pH 5.3) to adjust the concentration to 0.75%. To 2.7 ml of this albumin solution, 0.3 ml of a solution of a test compound in dimethyl sulfoxide was added and stirred. The reaction mixture was allowed to stand for 15 minutes to room temperature. After the solution was shaken for 2 minutes in a water bath at 67° C., the reaction was stopped by ice cooling. The temperature of the reaction mixture was raised to room temperature, and the absorbance depending on the white turbidity of water-soluble protein caused by heat coagulation was measured at 660 nm of wave length. The protein stabilizing effect of the compound of this invention was calculated by the following Formula.

As a reference compound, 2-(3,5-di-tert.-butyl-4-hydroxybenzylidene)-3,4-dihydro-4-methyl-3-oxo-2H-1,4-benzothiazine, which was described in Japanese Unexamined Patent Publication No. 287077/1989, was used.

$$\text{Protein stabilizing effect } (\%) = \frac{A_0 - A_1}{A_0} \times 100$$

$A_0$: absorbance in the case of absence of a test compound
$A_1$: absorbance in the case of presence of a test compound

Result

The experimental results were shown in Table 1.

TABLE 1

| Test compound | Concentration of test compound | Protein stabilizing effect |
| --- | --- | --- |
| Reference compound | $10^{-4}$M | −30.1% |
| Compound No.2-1 | $10^{-4}$M | 53.3% |
| Compound No.2-2 | $10^{-4}$M | 91.5% |
| Compound No.8-1 | $10^{-4}$M | 63.3% |
| Compound No.8-3 | $10^{-4}$M | 96.3% |

The compounds of this invention inhibited the heat coagulation of protein significantly and showed excellent protein stabilizing effect. But the reference compound did not show protein stabilizing effect, and a tendency to accerate the heat coagulation of protein was observed.

2. Suppressive Effect on Lipid Peroxide Formation

Experimental Method

In 0.04 M Tris buffer (containing 0.09 M of potassium chloride, pH 7.4) containing a test compound, microsomes of rat liver were reacted with ADP (13.2 mM), $Fe^{2+}$ (0.9 mM) and ascorbic acid (0.5 mM) for 15 minutes at 37° C. The amount of the produced lipid peroxide was measured by TBA method (Yagi et al., Biochem. Med., 15, 212 (1976)).

14
Result

The experimental results were shown in Table 2.

TABLE 2

| Test compound | Concentration of test compound | Suppressive effect on lipid peroxide formation |
| --- | --- | --- |
| Compound No.2-1 | $10^{-6}$M | 81.2% |
| Compound No.2-2 | $10^{-6}$M | 99.1% |
| Compound No.8-1 | $10^{-6}$M | 93.7% |
| Compound No.8-3 | $10^{-6}$M | 94.0% |

As shown in Table 2, each compound of this invention showed excellent suppressive effect on lipid peroxide formation.

As shown in the results of the above Pharmacological Tests, the compound of this invention has both protein stabilizing effect and suppressive effect on lipid peroxide formation and it is expected that the compound of this invention is excellent therapeutic agent for cataract.

INDUSTRIAL APPLICABILITY

This invention provides novel 3-oxo1,4-benzothiazine derivatives which have both protein stabilizing effect and suppressive effect on lipid peroxide formation, and are useful for treatment of cataract.

What we claim is:

1. A compound having the following formula (I) or a salt thereof,

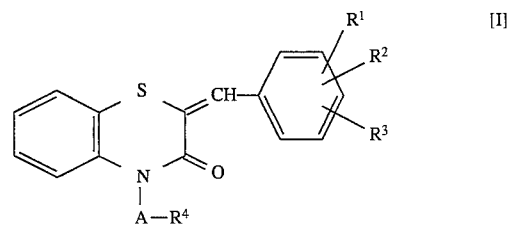

wherein
R[1] is hydroxy, lower alkanoyloxy, lower alkylsulfonyloxy, phenylsulfonyloxy, methylphenylsulfonyloxy, lower alkoxymethyloxy, benzoyloxy, benzyloxymethyloxy, tetrahydropyranyloxy or trimethylsilyloxy;

R[2] is lower alkyl;

R[3] is hydrogen, lower alkyl, hydroxy, lower alkanoyloxy, lower alkylsulfonyloxy, phenylsulfonyloxy, methylphenylsulfonyloxy, lower alkoxymethyloxy, benzoyloxy, benzyloxymethyloxy, tetrahydroxpyranyloxy, trimethylsilyloxy or lower alkoxy, and the said lower alkyl can be substituted by hydroxy, lower alkanoyloxy, lower alkylsulfonyloxy, phenylsulfonyloxy, methylphenylsulfonyloxy, lower alkoxymethyloxy, benzoyloxy, benzyloxymethyloxy, tetrahydropyranyloxy, trimethylsilyloxy, amino or lower alkylamino;

R[4] is carboxy, lower alkoxycarbonyl, phenyl lower alkoxycarbonyl, aminocarbonyl, lower alkylaminocarbonyl or phenyl lower alkylaminocarbonyl, and A is alkylene having 1 to 10 carbon atoms.

2. A compound as claimed in claim 1 and salts thereof, wherein R[1] is hydroxy or lower alkanoyloxy, and R[4] is carboxy or lower alkoxycarbonyl.

3. A compound as claimed in claim 1 and salts thereof, wherein R[1] is hydroxy or lower alkanoyloxy; R[3] is hydrogen or lower alkyl, and R[4] is carboxyl or lower alkoxycarbonyl.

4. A compound and salts thereof as claimed in claim 1 thereof, wherein $R^1$ is hydroxy or acetoxy; $R^2$ is methyl or tert.-butyl; $R^3$ is hydrogen, methyl or tert.-butyl; $R^4$ is carboxy, methoxycarbonyl or ethoxycarbonyl, and A is methylene or propylene.

5. A compound as claimed in claim 1 and salts thereof, wherein $R^1$ is hydroxy; $R^2$ is methyl or tert.-butyl; $R^3$ is hydrogen, methyl or tert.-butyl; $R^4$ is carboxy, and A is methylene or propylene.

6. 4-Carboxymethyl-2-(3,5-di-tert.-butyl-4-hydroxybenzylidene)-3,4-dihydro-3-oxo-2H-1,4-benzothiazine.

7. 4-(3-Carboxypropyl)-2-(3,5-di-tert.-butyl-4-hydroxybenzylidene)-3,4-dihydro-3-oxo-2H-1,4-benzothiazine.

8. 4-Carboxymethyl-3,4-dihydro-2-(3,5-dimethyl-4-hydroxybenzylidene)-3-oxo-2H-1,4-benzothiazine.

9. 2-(3-tert.-Butyl-4-hydroxybenzylidene)-4-carboxymethyl-3,4-dihydro-3-oxo-2H-1,4-benzothiazine.

10. A pharmaceutical composition comprising a compound as in claim 1 or salt thereof and a pharmaceutically acceptable carrier.

11. A method of treating a cataract comprising administering to a host exhibiting cataract formation, an effective amount of a compound or salt thereof as claimed in claim 1.

12. A therapeutic composition for instillation into the eye of a host for treatment of cataract formation comprising a compound or salt thereof as claimed in claim 1 in an effective amount, dissolved in an ophthalmologically acceptable carrier.

* * * * *